(12) United States Patent
Baykut

(10) Patent No.: US 8,921,780 B2
(45) Date of Patent: Dec. 30, 2014

(54) COMPACT ION MOBILITY SPECTROMETER

(71) Applicant: Bruker Daltonik GmbH, Bremen (DE)

(72) Inventor: Gokhan Baykut, Bremen (DE)

( * ) Notice: Subject to any disclaimer, the term of this patent is extended or adjusted under 35 U.S.C. 154(b) by 0 days.

(21) Appl. No.: 13/964,182

(22) Filed: Aug. 12, 2013

(65) Prior Publication Data
US 2014/0042315 A1 Feb. 13, 2014

(30) Foreign Application Priority Data

Aug. 10, 2012 (DE) .......... 10 2012 015 978

(51) Int. Cl.
*H01J 49/26* (2006.01)

(52) U.S. Cl.
USPC ............. 250/297; 250/281; 250/290

(58) Field of Classification Search
USPC ......... 250/281, 282, 290, 291, 292, 293, 294, 250/295, 296, 297, 298
See application file for complete search history.

(56) References Cited

U.S. PATENT DOCUMENTS

| | | |
|---|---|---|
| 2003/0155503 A1 | 8/2003 | Murphy et al. |
| 2008/0156978 A1 | 7/2008 | Shvartsburg et al. |
| 2008/0272285 A1 * | 11/2008 | Giannantonio et al. ...... 250/281 |
| 2010/0193678 A1 | 8/2010 | Clemmer et al. |
| 2011/0168882 A1 | 7/2011 | Hoyes |
| 2012/0261570 A1 * | 10/2012 | Shvartsburg et al. ......... 250/287 |
| 2013/0161508 A1 * | 6/2013 | Sapargaliyev et al. ........ 250/282 |

FOREIGN PATENT DOCUMENTS

| | | |
|---|---|---|
| GB | 2396742 A1 | 6/2004 |
| GB | 2447330 A1 | 9/2008 |
| WO | 2014021960 A1 | 2/2014 |

* cited by examiner

*Primary Examiner* — Nicole Ippolito
(74) *Attorney, Agent, or Firm* — Robic, LLP

(57) ABSTRACT

The invention relates to devices for measuring the mobility of ions in gases at pressures of a few hectopascal. To make the device more compact, drift regions are bent into curved shapes, which extend into the third dimension. Parts of the drift region may lie above others. Alternating directions of curvature in the curved shapes balance out different path lengths by passing through approximately equal drift distances on outer and inner trajectories. Ions are held near the axis of the curved drift region by sectional or permanent focusing. One possible shape is a double loop in the shape of a figure eight. The shape extends perpendicular to its plane of projection so that several double loops lie on top of each other. RF ion funnels or ion tunnels can keep the ions near the axis. Axial focusing may use a pseudopotential radial to the axis of the curved shape.

14 Claims, 4 Drawing Sheets

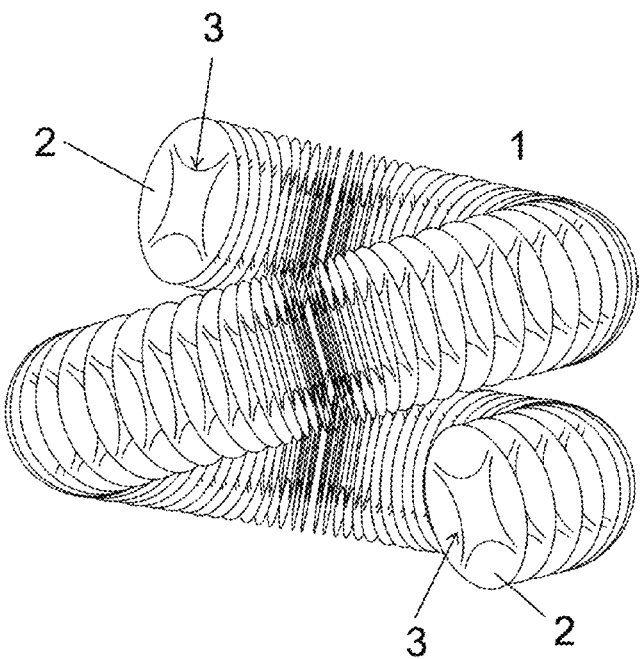
FIGURE 1
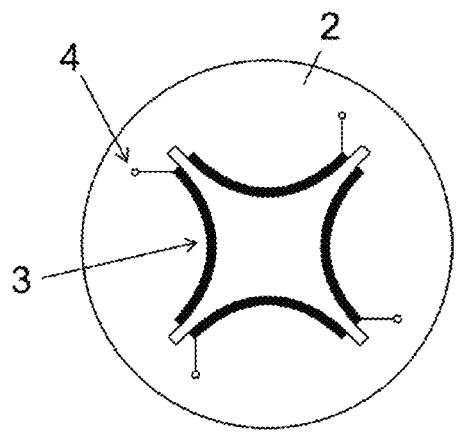 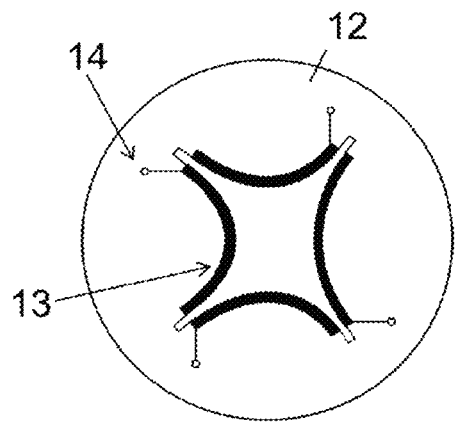
FIGURE 2A          FIGURE 2B

COMPACT ION MOBILITY SPECTROMETER

BACKGROUND OF THE INVENTION

1. Field of the Invention

The invention relates to devices for measuring the mobility of ions, particularly in gases at pressures of a few hectopascal.

2. Description of the Related Art

Isomers of the primary structure ("structural isomers") and isomers of the secondary or tertiary structure ("conformational isomers") possess different geometrical shapes but exactly the same mass. Mass spectrometry is therefore unable to detect that they are different. One of the most efficient methods of recognizing and distinguishing such isomers is to separate them by virtue of their ion mobility. A cell for measuring the ion mobility contains an inert gas (such as helium or nitrogen). The ions of the substance under investigation are usually pulled through the stationary gas by means of an electric field. The large number of collisions with the gas molecules leads to a constant drift velocity $v_d$ for every ionic species which is proportional to the electric field strength E: $v_d = M \times E$. The proportionality factor M is called the "ion mobility". The ion mobility M is a function of the temperature, gas pressure, type of gas, ionic charge and, in particular, the collision cross-section. Isomeric ions of the same mass but different collision cross-sections possess different ion mobilities. Isomers with the smallest geometry possess the largest mobility M and therefore the largest drift velocity $v_d$ through the gas. Protein ions which are unfolded undergo more collisions than tightly folded proteins. Unfolded protein ions therefore arrive at the end of the cell later than folded ions of the same mass.

A variety of information can be obtained from measurements of the ion mobility M. Measurements of the relative ion mobility are frequently used to investigate conformational changes or merely to discover the existence of different isomeric structures in a mixture. Ions with the same mass-to-charge ratio m/z but different conformation can be separated from each other relatively easily. It is even possible to calculate the absolute collision cross-sections from well reproduced measurements with helium as the gas. Specific folding forms can be confirmed in turn from the accurate collision cross-sections.

Knowledge of the mobility of ions has become more and more important in chemical and biological research, and devices for measuring ion mobility have therefore been incorporated in mass spectrometers in order to combine measurements of the mass-to-charge ratio of ions with measurement of collision cross-sections.

For couplings with mass spectrometers, a pressure range of 500 to 2000 pascals has been adopted almost universally for the mobility drift region; the drift region is 40 centimeters up to two meters and more, and electric field strengths of 1000 to 5000 volts per meter are applied. In this pressure range, the drifting ions form almost no complexes with other substances, so the mobilities of the ionic species can be measured without interferences. In long drift regions, the ions also diffuse apart in the radial direction over long distances, and therefore quite large diameters have to be chosen for long drift regions.

The ions are usually introduced into the drift region in the form of temporally short ion pulses, causing them to adopt the shape of spatially small ion clouds, which are pulled through the drift region by the electric field. These ion clouds are subject to diffusion in the gas of the drift region. The diffusion takes place in both the forward and the backward direction, and also transverse to the drift region. The mobility-resolving power $R_{mob}$ (mobility resolution for short) is predominantly determined by this diffusion broadening of the ion clouds, especially for long drift regions and low electric field strengths; all other influences, such as the space charge, tend to be infinitesimally small. The mobility resolution $R_d$, which is calculated solely from the diffusion broadening of the mobility signal, is given by the equation:

$$R_d = \frac{1}{4} \sqrt{\frac{zeEL_d}{kT\ln 2}}$$

where z is the number of elementary charges e, E the electric field strength, $L_d$ the length of the drift region, k the Boltzmann constant and T the temperature. It can be seen that the diffusion-limited resolution increases with the field strength E, and particularly with the length $L_d$ of the drift region also, albeit only as the square root in both cases. Multiply charged ions can be resolved better than singly charged ones because the resolution increases as the square root of the charge number. The mobility resolution is defined as $R_{mob}=M/\Delta M$, where $\Delta M$ is the width of the ion signal of the mobility M at half maximum, measured in units of the mobility. Since the mobility resolution $R_{mob}$ depends not only on the diffusion, but also on the finite width of the pulse and on the space charge, for example, it normally has a slightly smaller value than $R_d$.

Mobility resolutions are generally not very high when compared with mass resolutions in mass spectrometry. Commercial ion mobility spectrometers have resolutions of $R_{mob}=10$ to $R_{mob}=40$. With a mobility resolution of $R_{mob}=40$, two ionic species whose collision cross-sections differ by five percent can be readily separated. Specialized research groups have so far been able to achieve maximum mobility resolutions of $R_{mob}=200$, with drift lengths of approximately four to six meters and field strengths of 2000 volts per meter or more, making it possible to differentiate between ionic species whose mobilities differ only by around one percent. Those ion mobility spectrometers whose resolution is above $R_{mob}=60$ shall be called "high-resolution" here.

In long drift regions, the ion clouds diffuse very expansively in the radial direction. It has therefore proved expedient to return the ions closer to the axis at certain intervals, every two meters, for example. This can be achieved by ion funnels, which are already known. These ion funnels do not measurably impair the mobility resolution.

It is also possible to keep the ions in the mobility cell on axis by means of RF-generated pseudopotentials. Such an arrangement, installed into a mass spectrometer, was described by A. V. Loboda, U.S. Pat. No. 6,744,043 B2 (2004). The principle of axial focusing of ions by pseudopotentials in a drift region, where the ions are pulled through a damping gas in a DC field, is already disclosed in the patent specification Thomson et al. U.S. Pat. No. 5,847,386 (1998), although there the mechanism was not claimed for the measurement of mobility. The Loboda patent specification, like Thomson et al., proposes an RF ion guide with radial collision focusing for the drift region; the ion guide can be constructed as an RF multipole rod system or as a system of rings.

High-resolution ion mobility spectrometers have the disadvantage of being several meters long. Such a solution is not acceptable for instruments marketed commercially. The research group of David E. Clemmer therefore proposed that the drift region be formed into a closed loop (a type of circular trajectory) with several ion funnels inserted. The ions should enter the circular trajectory via an ion gate, pass through several times and then leave again in a further gate. See also documents U.S. 2010/0193678A1 (D. E. Clemmer et al.), U.S. 2009/0189070 (D. E. Clemmer et al.) and U.S. 2011/0121171A1 (D. E. Clemmer et al.) for this. The research group incorrectly coined the name "Ion Cyclotron Mobility Spectrometry" for this, but the group itself expects relatively major technical problems with this solution. The presence of the gates limits the mobility region because, although it can be extended to a longer drift path and thus higher resolution by means of several orbits of the mobility region, only the region of one single orbit can be measured. The technical design of the gates is difficult if the mobility resolution is to be maintained. A particularly difficult problem which has to be expected, however, is that ions which get onto an outer trajectory by diffusion, and circulate there, will fall behind ions on an inner trajectory due to the longer drift paths and the lower electric field strength. Even if ion funnels are inserted after each quarter of the circular trajectory, the mobility resolution is reduced so much that the value of the proposal must be called into question.

For the construction of compact mobility spectrometers in particular, one therefore has to look for a solution which shortens the overall length, i.e. decreases the "footprint" of the device, but does not diminish the mobility resolution.

We mention only briefly here that for many years arrangements of mobility spectrometers have been known where the isomers are subsequently analyzed with a high-resolution time-of-flight mass spectrometer with orthogonal ion injection, the aim being to obtain mass spectra and mobility spectra of the ion mixtures at the same time. Ion mobility drift cells combined with orthogonally accelerating time-of-flight mass spectrometers have been known from textbooks for forty years.

It is not necessary for the ions to be injected into the drift regions in the form of short ion pulses. The patent application DE 10 2008 025 972.1 (K. Michelmann), equivalent to GB 2 460 341 A or U.S. 2009/0294647 A1, uses an ion mobility spectrometer, for example, which operates with an analog-modulated ion current without ion pulses, the mobility spectrometer being coupled to a mass spectrometer. These arrangements are subject to diffusion broadening of the ultimately obtained mobility spectra in the same way as the ion mobility spectrometers operated with ion current pulses.

Mass spectrometers can only ever determine the ratio of the ion mass to the charge of the ion. In the following, the term "mass of an ion" or "ion mass" always refers to the ratio of the mass m to the number z of elementary charges of the ion, i.e. the charge-related mass m/z. The quality of a mass spectrometer is essentially determined by the mass resolution, amongst other criteria. The mass resolution is defined as $R_{mass}=m/\Delta m$, where $R_{mass}$ is the resolution, m the mass of an ion, measured in units of the mass scale, and $\Delta m$ the full width of the mass signal at half maximum, measured in the same units.

SUMMARY OF THE INVENTION

The invention is based on the finding that drift regions can be bent into curved shapes which are arranged not only in one plane, but can also extend into the third dimension. This enables compact configurations to be produced. Curves can lie in tiers one above the other in a dimension perpendicular to the projected area, for example. The drifting ions here can be kept in the axis of the curved shapes by permanent or repeated RF focusing so that all ions cover the same distances. It is also possible for ions which are at a distance from the axis due to diffusion processes to travel outer and inner trajectories alternately in specially shaped drift regions with opposing curvatures even without RF focusing, in order to balance out the differences in distance and differences in the electric field strengths. The mobility resolution is not significantly affected in either case.

One advantageous example for a curved shape with opposing curvatures is the convolution to form double loops, each in the form of a figure eight. These double loops do not turn back on themselves in one plane, but wind perpendicular to their plane in space, for example in such a way that the double loops lie spatially on top of each other in tiers. Electric arcing between loops or windings lying on top of each other due to a voltage difference between two tiers can be prevented by defining the minimum distance between the tiers according to the voltage to be applied. The tiers of loops or windings can also be insulated from each other by appropriate layers or sheaths.

The balancing out of the distances by opposing curvatures can also be combined with RF focusing. RF ion funnels or RF ion tunnels inserted at suitable positions can return the ions to the axis again. Suitable positions for these ion funnels or ion tunnels are reasonably straight sections of drift region, in the cross-over region of the double loops, for example.

Particularly advantageous is the permanent radial focusing of the drifting ions into a narrow trajectory near the axis of the curved shape by means of a pseudopotential, which acts radially to the axis of the curved drift regions and perpetually drives the ions back to the center. In conjunction with the drift gas, which damps all oscillatory motions in the potential channel, the ions remain in a narrow trajectory during their drift. An RF-generated pseudopotential with superimposed DC drawing field can be generated by convoluted and segmented multipole rod systems, by RF ring diaphragm systems, or by double or multiple helices of resistance wire.

The ions are usually pulled through a stationary drift gas in these arrangements. But the convoluted curved shapes can also be designed as a tube with inner electrodes, and the gas can be made to flow in this tube in order to shorten the distance or increase the mobility resolution, for example.

BRIEF DESCRIPTION OF THE DRAWINGS

FIG. 1 is a schematic representation of a helically wound drift region (1), which is constructed from apertured diaphragms (2), where the openings of the apertured diaphragms (2) are each surrounded by four hyperbolic electrodes (3), which are insulated from each other. A radially focusing pseudopotential is generated by alternating phases of an RF voltage with a frequency of around one megahertz and a voltage of a few hundred volts at the quadrupole electrodes of each apertured diaphragm; the electric drawing field for the mobility motion is generated by superimposed DC potentials, which change uniformly from apertured diaphragm to apertured diaphragm. The helically wound drift region allows a high mobility resolving power to be achieved within a compact configuration. With this configuration, three windings with a radius (to the drift axis) of around 20 centimeters can realize drift regions four meters long on a square base area with an edge length measuring only around 50 centimeters, for example. A mobility drift cell with these dimensions can be easily placed even on small laboratory benches.

FIGS. 2a and 2b are schematic representations of apertured diaphragms (2, 12) with four hyperbolic electrodes (3, 13) and contacts (4, 14), which can be used to set up the helically wound drift region (1) according to FIG. 1. The apertured diaphragm according to FIG. 2a with symmetric electrodes does not force the ions into the axis of the drift region; this requires a slightly distorted apertured diaphragm with asymmetric electrodes according to FIG. 2b in a special embodiment. The required shape of the asymmetric electrodes depends on the radius of the drift region.

DETAILED DESCRIPTION

Figure 3:
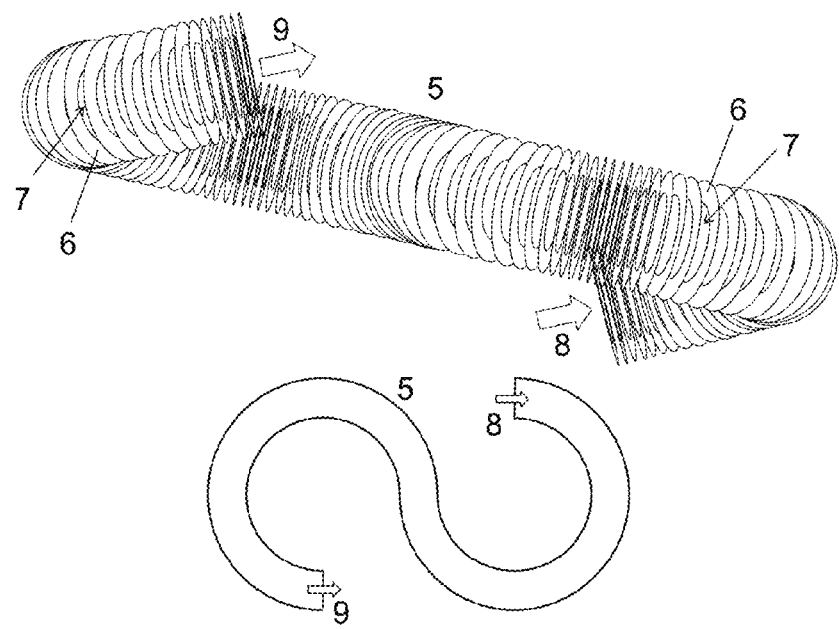
FIG. 3 is a schematic representation of an S-shaped section (5) of a drift region approximating a figure eight shape and made up of apertured diaphragms (6) with round apertures (7). An extension of this section can be used to construct a drift region made of folded figure eights lying on top of each other, as shown in FIG. 4. Radial focusing, as in FIG. 1, does not take place in the apertured diaphragms here; however, ions which have diffused outwards from the axis are brought into trajectories of approximately equal length by the alternating direction of the curvature. This effect is possible in this S-shaped section (5) because the ions which fly into this drift region (8) cover two opposing three-quarter sections of a circular trajectory and then leave the drift region (9).

The invention is based on the finding that, in order to design a compact device, drift regions can be bent into curved shapes, which may also extend into a third dimension. Parts of the drift region can lie in tiers one above the other. Ions which have moved away from the axis by diffusion processes can balance out different path lengths with the aid of alternating curvature directions by passing through approximately equal drift distances on outer and inner trajectories. Alternatively, ions can be held along the axis of the curved drift region by sectional or permanent focusing. This allows the overall length to be reduced without the mobility resolution suffering greatly. One example for a curved shape with alternating direction of curvature is convolution to form a double loop in the shape of an eight. The eight does not turn back on itself, but shifts perpendicular to its plane of projection in such a way that several double loops come to lie on top of each other. RF ion funnels or ion tunnels inserted at suitable positions can keep the ions close to the axis. Sectional or permanent axial focusing can be achieved by pseudopotentials acting radially to the axis of the curved shape.

The invention follows generally the proposal of the Clemmer research group (referenced above) to bend the drift regions in order to reduce the overall length, but overcomes certain technical drawbacks of that prior art strategy. The gates required by Clemmer et al. can be avoided completely if the curved shapes do not turn back on themselves in one plane, but use the third spatial dimension in such a way that a compact configuration is created. Curves can lie on top of each other in tiers, for example. Curvatures of alternating direction can balance out the fact that ions on outer trajectories fall behind those on inner trajectories on the statistical average; it is also possible to keep the ions close to the axis by pseudopotentials over the entire drift region or repeatedly in sections of the drift region.

One embodiment of the invention consists in bending the drift regions helically into circles, as shown in FIG. 1. Here the ions must be kept in the axis of the drift region by permanent or repeated focusing. This can take place by collision focusing, as is known from RF ion guides. This requires that a radial pseudopotential is established in the drift region in order to drive the ions back to the axis. As is known from RF ion guides, a pseudopotential can be generated by multipole fields, for example by quadrupole or hexapole rod systems. A potential channel is thus created in the longitudinal direction of the drift region. All oscillatory motions in this potential channel are damped in the drift gas so that the ions are reliably kept in a focusing axis.

The pole rods must be segmented here in order to generate the DC voltage gradient for the drift of the ions. The series of apertured diaphragms in FIG. 1 with insulated edge electrodes represents a very fine segmentation. It is possible to produce the apertured diaphragms (2) from non-conducting material with hyperbolic conducting metal electrodes (3). These electrodes can generate the quadrupole field. The apertured diaphragms with the electrodes can be produced from the material for electric circuit boards or from ceramics, for example.

If the electrodes of the apertured diaphragms are symmetric, as shown in FIG. 2a, the focusing axis of the helical drift region in FIG. 1 does not coincide with the geometric axis of the drift region, which can be defined via a line which connects the centers of the apertured diaphragms. A distortion of the shape of the electrodes, as shown in FIG. 2b, can make the ion trajectory coincide with the axis of the drift region by means of the asymmetric distribution of the pseudopotential. The voltage is connected at the contact points (4, 14).

Permanent radial focusing of the drifting ions to a trajectory near the axis of the curved shape can also be achieved by means of a drift region which is constructed from parallel ring diaphragms with circular apertures, for example, by applying the two phases of an RF voltage in turn to the ring diaphragms. Here too, a pseudopotential which drives the ions away from outer trajectories and back to the vicinity of the axis of the drift region is generated.

The drift region here does not have to be circular, but can be any shape, for example a square or hexagon with rounded corners. The shape is, however, curved into the third dimension is such a way that it forms a series of tiers. A 360° "spiral", as shown in FIG. 1, can be considered to be a tier. The exact meaning of the designation "tier" can be defined separately for all conceivable embodiments.

Furthermore, when the drift path is bent into curved shapes, it is possible to exploit the fact that ions which are outside the axis due to diffusion processes in the curved drift region will travel approximately equal distances on outer and inner trajectories with the aid of a series of drift regions with opposing curvature. This applies primarily when only a small diffusion drift takes place due to a relatively high attracting voltage. The differences in distance and also the differences in the electric field strengths are then balanced out to a large extent.

Figure 4:
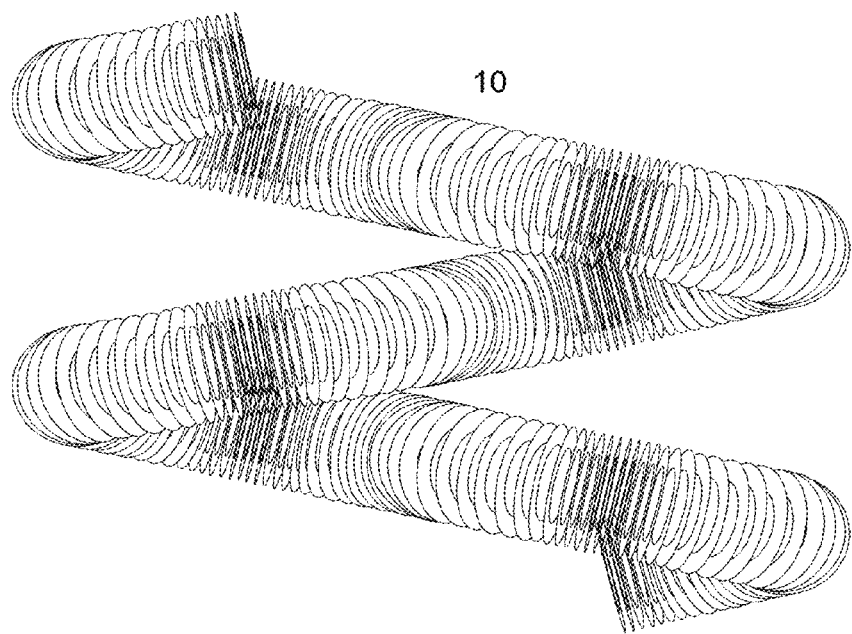
FIG. 4 shows an arrangement (10) of layered, curved drift regions, each approximating a figure eight, which can be constructed by modifying and extending the section (5) according to FIG. 3.
Figure 5:
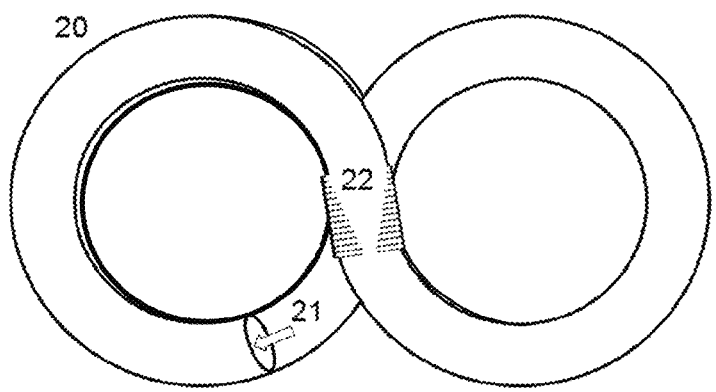
FIG. 5 schematically depicts a top view of a drift region (20) which is wound to form a stacked figure eight and contains an ion funnel (22) in each eight, at one of the two relatively straight cross-over sections where the direction of curvature changes. This brings the outward diffusing ions close to the axis again and again. The top and bottom eights contain an entrance (21) and an exit (not visible) for the ions.

One advantageous embodiment for a curved shape with opposing curvatures is bending into double loops, each approximating a figure eight. These double loops should not turn back on themselves, but extend in a direction perpendicular to their plane in space so that the double loops come to lie on top of each other in tiers, as shown in FIG. 4. RF ion funnels or RF ion tunnels inserted at suitable positions can keep the ions near the axis. As depicted in FIG. 5, reasonably straight drift path sections are suitable locations for these ion funnels or ion tunnels, for example approximately straight drift paths in the cross-over region of the double loops. Those skilled in the art will understand that the number of figure eight shapes used will depend on the overall length desired for the drift chamber.

In each of the foregoing embodiments, the ions are typically pulled through a stationary drift gas. The convoluted curved shapes can, however, also be designed as a tube with inner electrodes and the gas can be made to flow in this tube. This can shorten the distances required for mobility resolution, for example, or the mobility resolution can be increased.

Figure 6:
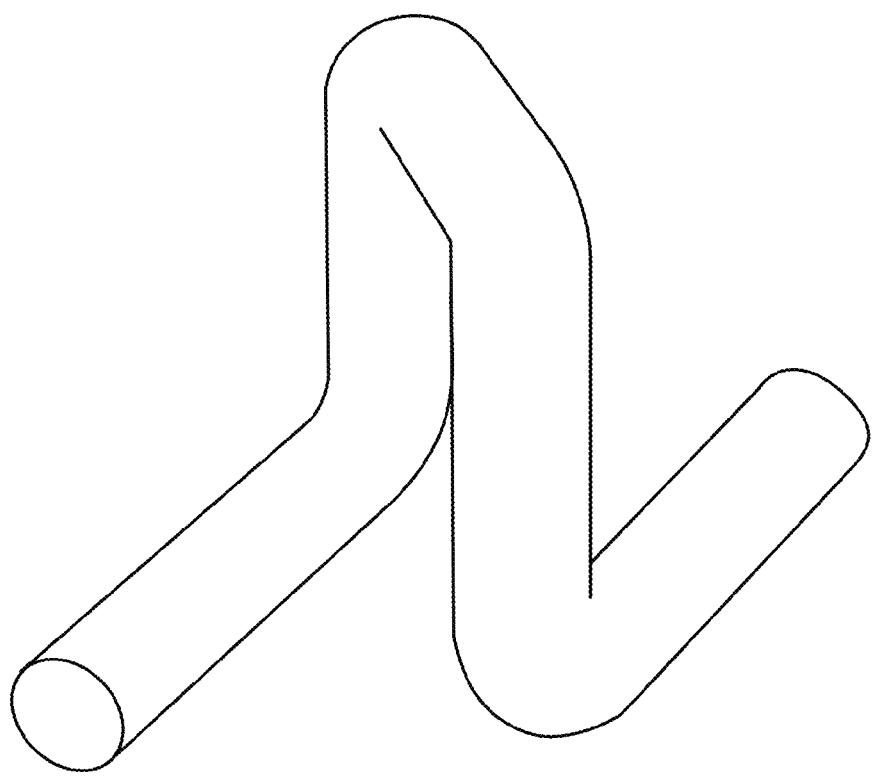
FIG. 6 depicts a curved shape which does not turn back on itself in the base plane, but provides a compact configuration by extending into a third dimension.
Figure 7:
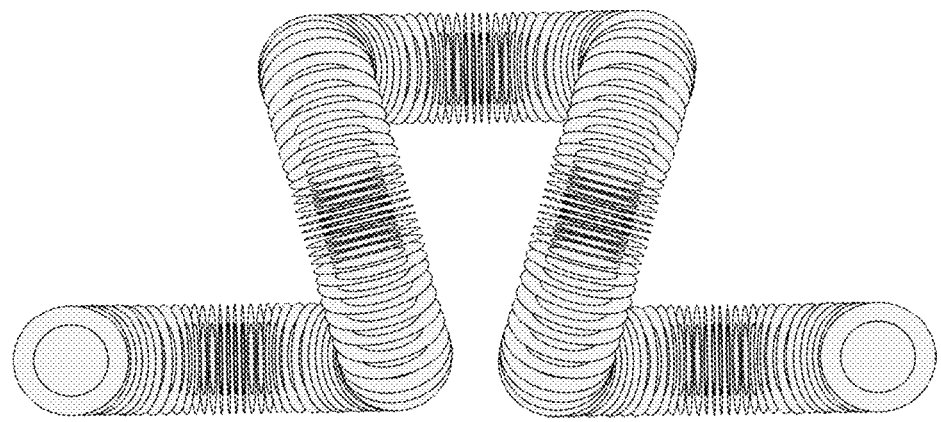
FIG. 7 also provides a curved shape which extends through all three spatial dimensions.

It is also possible to design drift regions which are completely different to those described here. FIGS. 6 and 7 show curved shapes which do not turn back on themselves in their projection onto a base area. The drift region can also be constructed from apertured diaphragms, whose apertures increase along the drift region in order to keep the ion clouds, which are expanding due to diffusion, in the drift region. It is also possible not to construct the drift regions from apertured diaphragms. A drift region can be constructed with double or multiple helices of resistance wire, for example. It is also possible to use tubes which are coated on the inside with resistance material. All these solutions shall be protected by this application as long as they are drift regions in the form of curves which extend over all three spatial dimensions.

The compact form described for ion mobility spectrometers operated at low pressures can also be applied for atmospheric pressure ion mobility spectrometers. In this case drift regions with opposing curvature are particularly advantageous. When the drift path is bent into curved shapes, ions which are outside the axis in the curved drift region due to diffusion processes will travel approximately equal distances on outer and inner trajectories with opposing curvature. This applies because in the gas of relatively high pressure only a small diffusion drift takes place. The differences in distance and also the differences in the electric field strengths are then balanced out to a large extent.

The invention claimed is:

1. Device for the separation of ions according to their ion mobility with a drift region in which the ions are pulled through a gas by means of electric fields, wherein the drift region is bent into a curved shape which extends over three spatial dimensions and comprises opposing curvatures such that ions at a distance from the axis travel alternately on outer and inner trajectories.

2. Device according to claim 1, wherein the curved shape of the drift region turns back on itself in the projection onto a base area, and at least parts of the drift region come to lie adjacent to each other in a third dimension.

3. Device according to claim 2, wherein the drift region is designed as a tube with inner electrodes and gas flows in the tube.

4. Device according to claim 2, wherein the drift region has the shape of a figure eight layered in tiers.

5. Device according to claim 1, wherein the drift region is formed by a row of apertured diaphragms.

6. Device according to claim 5 with a voltage supply which is used to supply the apertured diaphragms alternately with the two phases of an RF voltage.

7. Device according to claim 5, wherein openings of the apertured diaphragms are framed by electrodes which are all insulated from each other, these electrodes being used to generate a multipole RF field in the drift region by applying suitable RF voltages in order to keep the ions in a narrow trajectory.

8. Device according to claim 7, wherein the electrodes have a hyperbolic shape.

9. Device according to claim 7, wherein the insulated electrodes are shaped in such a way that the ions are kept near the axis of the drift region.

10. Device according to claim 5, wherein openings of the apertured diaphragms are circular.

11. Device according to claim 1, wherein ion funnels or ion tunnels are installed in the drift region.

12. Device according to claim 5, wherein openings of the apertured diaphragms increase in size in the direction of the drift.

13. Device according to claim 1, wherein the drift region is formed by at least two resistance wires wound into a double helix.

14. Mass spectrometer which is coupled with a device for ion mobility separation according to claim 1.

* * * * *